United States Patent [19]

Rosch et al.

[11] Patent Number: 4,585,450
[45] Date of Patent: Apr. 29, 1986

[54] REFASTENABLE TAPE SYSTEM FOR DISPOSABLE DIAPERS AND SIMILAR GARMENTS

[75] Inventors: Paulette M. Rosch, Outagamie County; Thomas J. Kopacz, Winnebago County, both of Wis.

[73] Assignee: Kimberly-Clark Corporation, Neenah, Wis.

[21] Appl. No.: 728,375

[22] Filed: Apr. 29, 1985

[51] Int. Cl.$^4$ ............................................. A61F 13/16
[52] U.S. Cl. ................................................. 604/390
[58] Field of Search ................................ 604/390, 389

[56] References Cited

U.S. PATENT DOCUMENTS

| | | | |
|---|---|---|---|
| 4,127,132 | 11/1978 | Karami | 604/390 |
| 4,144,887 | 3/1979 | Milnamow | 604/390 |
| 4,178,933 | 12/1979 | Nemeth | 604/390 |
| 4,227,530 | 10/1980 | Schatz | 604/390 |
| 4,345,597 | 8/1982 | Tritsch | 604/390 |

Primary Examiner—John D. Yasko
Attorney, Agent, or Firm—Paul A. Leipold; Donald L. Traut; J. J. Duggan

[57] ABSTRACT

A refastenable tape member (20) for disposable garments comprising a stationary release element (50) secured to the garment, a secondary tape element (30) including an adhesive layer (33) with a portion (34) adhered to the garment and another portion (35) free thereof, and a primary tape element (40) having a lower surface (44) with a major portion (A) releasably joined to the secondary tape element and a minor portion (B) adhesively bonded to the secondary tape element. The primary tape element (40) has an adhesive layer (43) which is releasably joined to the stationary release element (50) when in a storage position. To effect the first closure of the garment, the primary tape element (40) is separated from the release element (50); the adhesive bond between the secondary and primary tape elements (30, 40) along minor portion (B) assures dependable separation of the primary tape element (40) from the release element (50) for this purpose. The secondary tape element (30) is used for second and subsequent closures of the garment.

8 Claims, 5 Drawing Figures

U.S. Patent   Apr. 29, 1986   Sheet 2 of 2   4,585,450
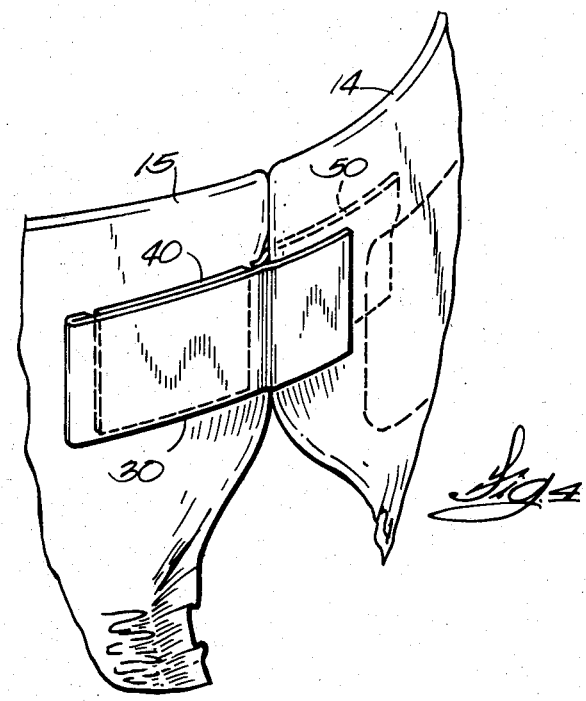
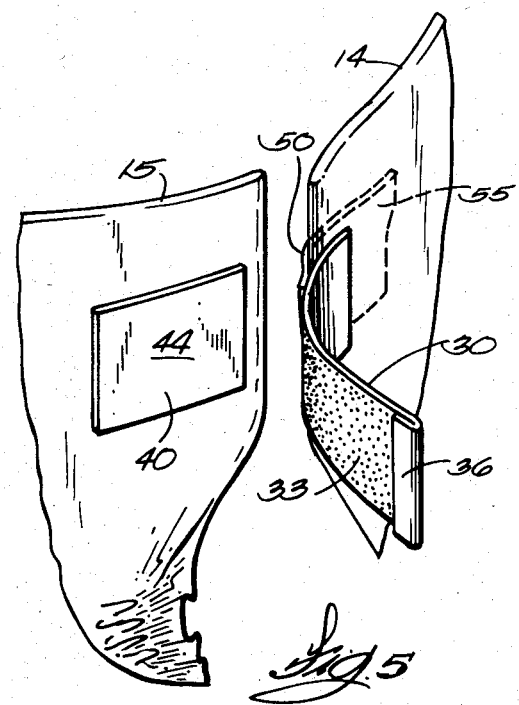

REFASTENABLE TAPE SYSTEM FOR DISPOSABLE DIAPERS AND SIMILAR GARMENTS

TECHNICAL FIELD

The present invention relates to tape fastening systems for disposable diapers and similar garments, more specifically to tape systems that provide for more than a single closure or fastening of a garment.

BACKGROUND ART

Disposable diapers of the type widely used today, such as those manufactured and sold by the assignee of this application, generally comprise a three layer composite structure including a liquid-permeable bodyside liner, a liquid-impermeable outer cover and a batt of absorbent material sandwiched between the liner and the outer cover. The diapers have front and rear panels joined together by a crotch section, and may be made in a rectangular or hour glass shape. The front and rear panels each have waist portions that encircle an infant's body and are overlapped and joined together to hold the diaper in place. In order to eliminate the need for pins or other mechanical fasteners to join the waist portions together, which would pose a danger to the infant, and so as to provide a complete garment that is ready for use without the need for additional fastening devices, disposable diapers have included pressure sensitive adhesive tabs as fastening means for securing the front and rear panels together about the waist of an infant.

At the inception of disposable diapers as commercial products, the most prevalent fastening means was a flexible tab attached to each corner of either the front or rear panel of the diaper (generally the rear panel) consisting of a strip of flexible material carrying a layer of pressure sensitive adhesive on one surface. An end portion of the tab was adhered to the outer surface of the panel and a free end portion extended beyond the side edge of the garment. The free end portion was covered with a release liner to protect the pressure sensitive adhesive. When the garment was ready to be applied, the release liner was removed from each fastening tab so as to expose the pressure sensitive adhesive along the free end portion of each tab, and the free end portion was then secured to the outer surface of the other panel of the diaper after the front and rear panels were overlapped.

The foregoing prior fastening system provided a convenient and secure system for fitting a disposable diaper about an infant and is still widely used today. However, it suffers the disadvantage of resulting in only a single-closure fastening system. The liquid impermeable outer cover of a disposable diaper is a plastic film, such as polyethylene or polypropylene, that of necessity is quite thin, such as only about one or two mils thick. The pressure sensitive adhesive used for the fastening tapes is generally an aggressive adhesive with good adhesion to the material of the outer cover in order to provide for secure fastening. When one attempts to remove the fastening tabs from a diaper after they have been secured in place, the outer cover of the body panel of the diaper to which the adhesive is secured can be ruptured or stretched or in any event damaged sufficiently to make reuse of the diaper undesirable. This, for example, prevents a person from checking the diaper after it has been on for awhile and refastening it if it has not been soiled.

To meet this latter problem of single closure adhesive tape fastening systems, there have more recently been developed adhesive fastening tape systems that enable two or more closures of the diaper. These constructions utilize pressure sensitive adhesive fastening tabs that have primary and secondary fastening tapes; the primary tape is used for the first closure of the diaper, and the secondary tape for the second and any subsequent closure of the diaper. A particularly useful structure for a refastenable tape system is that currently employed in commercial products made by the assignee of this application. Refastenable tape tabs are secured to each side of the rear panel of the diapers near the upper margin thereof. Each refastenable tab includes a secondary fastening tape having a first portion secured to the exterior of the outer cover of the diaper and a second portion extending beyond the side margin of the diaper, the outermost extremity of which has a finger tab; a release element adhered to the liner of the diaper and having a second surface which is releasable relative to pressure sensitive adhesive; a primary fastening tape having a first surface releasably joined to the adhesive of the secondary element and carrying pressure sensitive adhesive on its opposite surface, the outer extremity of which has a tab extending beyond the tab of the secondary element. During manufacture of the diaper, the primary tape is releasably joined to the exposed surface of the release element along the bodyside liner of the diaper, with the second or free end portion of the secondary tape folded over and releasably joined to the second surface of the primary tape. The first closure of the diaper is made by peeling away the primary fastening tape from the release element and joining the exposed adhesive thereof to the outer cover of the front panel of the diaper; removal of the primary fastening tape from the release element is facilitated by the finger tab of the primary element. The secondary fastening tape is positioned at the front of the diaper and overlies the primary tape that forms the initial closure. When it is desired to open the diaper, the secondary tape is peeled from the primary tape, which is easily accomplished since the adhesive layer of the secondary tape is releasably joined to the second surface of the primary tape; lifting the secondary tape from the primary tape also is facilitated by the finger tab at its outer end. The second closure of the diaper is thereafter made by adhering the pressure sensitive layer of the free end portion of the secondary tape to the exposed second surface of the primary tape or to a section of the outer cover of the diaper, as desired; the former method, when employed, enables several more refastenings of the diaper since removal of the secondary tape from the release surface of the primary tape does not rupture the outer layer of the diaper.

Multiple closure or refastenable tape systems for diapers and other disposable garments thus have two requirements that must be met for proper operation. Firstly, the adhesive member which is to form the initial closure, such as the primary fastening tape described above, must release dependably from the element to which it is secured when in a storage or closed position. Secondly, the adhesive member forming the initial closure must remain bonded to the adhesive layer of the member that is to be used for the second and subsequent closures of the garment firmly enough to provide a good initial closure.

SUMMARY OF THE INVENTION

The present invention was developed in order to satisfy the foregoing criteria of refastenable tape systems for diapers and other disposable garments. A refastenable tape member is provided having primary and secondary closure tape elements wherein the primary closure tape element has a surface with a major portion releasably joined to pressure sensitive adhesive of the secondary closure tape element and a minor portion that is adhesively joined to pressure sensitive adhesive of the secondary closure tape element. This construction ensures dependable release of the primary closure tape element from its storage position and enhancement of the strength of an initial closure made with the refastenable tape member.

DESCRIPTION OF THE DRAWINGS

The present invention is described below, as required by 35 U.S.C. §112, in sufficient detail to enable those skilled in the art to practice the invention and to set forth the presently-contemplated best modes for its practice by reference to the following drawings, in which:

FIG. 4 is a perspective view of a portion of a diaper showing the initial closure made with a refastenable tape member of this invention; and FIG. 5 is a perspective view similar to FIG. 4 illustrating opening of the initial closure of FIG. 4.

BEST MODES FOR CARRYING OUT THE INVENTION

(a) Background Description

Figure 1:
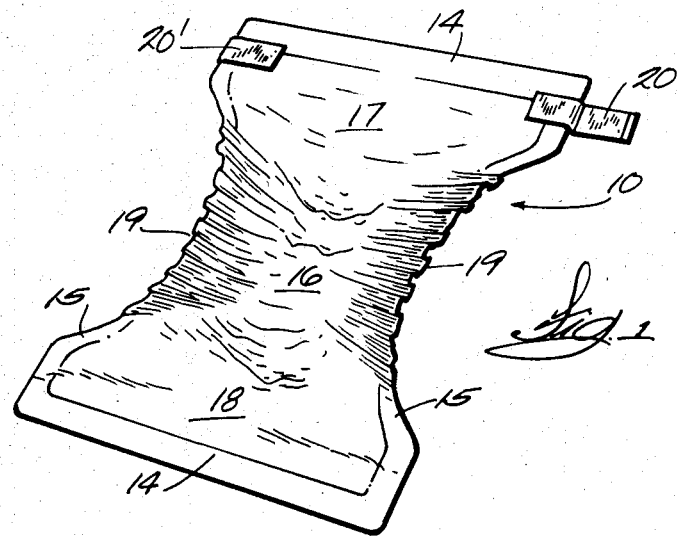
FIG. 1 is a perspective view of a diaper including refastenable tape members of this invention.

FIGS. 1–5 illustrate a disposable diaper 10 comprising a liquid-permeable bodyside liner 11, a liquid-impermeable outer cover 12, and an absorbent batt 13 secured therebetween. The liner 11 and cover 12 are larger than the absorbent batt 13 and have end marginal portions 14 extending beyond the ends of the batt and side marginal portions 15 extending beyond the sides of the batt, the liner 11 and cover 12 being secured to each other along the end and side marginal portions. Conventional materials are used for these elements of the diaper 10. The bodyside liner 11 may be any soft, flexible porous sheet which passes fluids therethrough and may comprise a nonwoven web or sheet of polyolefin fibers such as polypropylene, wet strength tissue paper, a spun woven filament sheet, etc. It may be treated with a surfactant to aid in liquid transfer. The cover 12 is a liquid-impermeable layer and may comprise a thin web or sheet of plastic film such as polyethylene, polypropylene, polyvinyl chloride or the like; it may be transparent or have an embossed or matte surface to be opaque. The absorbent batt 13 may be of any suitable material, generally cellulosic material such as an air-formed batt of wood pulp fibers commonly known as "fluff", and may include compounds to increase its absorbency.

The liner 11, cover 12 and batt 13 may be combined in any suitable manner to form the finished diaper. The elements can be bonded to one another by means of strips or patterns of hot melt or pressure sensitive adhesive, overall or patterned heat sealing, strips of double face pressure sensitive adhesive tape, etc. A particularly effective bonding system comprises spaced parallel lines of hot melt adhesive on the interior surface of the outer cover 12, with the absorbent batt bonded to the cover 12 along sections of the lines of adhesive and the liner 11 bonded to the cover 12 along other sections of the lines of adhesive within the end and side marginal portions 14 and 15 outside the batt.

The diaper 10 is of a generally hourglass or I shape including a central narrowed crotch section 16 connecting a rear panel 17 to a front panel 18. Elongate elastic means may be secured in place adjacent the absorbent batt 13 on each side thereof to develop gathered elastic leg portions 19 in the crotch section that are conformable with an infant's legs. The diaper 10 is fitted to an infant with bodyside liner 11 against the child's skin; end marginal portion 14 of the front panel 18 encircles part of the infant's waist and end marginal portion 14 of the rear panel 17 encircles the rest of the infant's waist and is overlapped and joined to the front panel to hold the diaper in place.

The structure of diaper 10 as described to this point forms no part of the present invention and further details of its construction may be had by reference, for example, to U.S. Pat. No. 4,050,462. The diaper 10 is illustrative only, and the present invention may be used with diapers of other constructions and other shapes such as rectangular diapers.

(b) Structural Description

In accordance with this invention, the diaper 10 includes refastenable tape members 20, illustratively shown as being secured to the rear panel 17 near the end margin 14 thereof. In FIG. 1, the right hand tape member 20 is depicted in an open position and the left hand tape element 20' is shown in a closed or storage condition. Both tape members 20 and 20' are of the same construction, which is illustrated in detail in FIGS. 2 and 3.

Each refastenable tape member 20 comprises three elements: a foldable secondary closure tape element 30, a primary closure tape element 40 and a stationary release element 50.

The secondary closure tape element 30 is made of an elongate backing strip of flexible material, such as thermoplastic film or paper, having a first surface 32 that is covered with a pressure sensitive adhesive layer 33. A first portion 34 (FIG. 3) of the tape element 30 is adhesively bonded by means of part of the pressure sensitive adhesive layer 33 to the exterior of the outer cover 12 of the diaper. A second portion 35 (FIG. 3) of the element 30 extends beyond the side edge of the diaper when in the open position of FIG. 2 to form a free end portion of the element. The second portion 35 of the element 30 is to be foldable about the side edge of the diaper between the closed or storage position as illustrated by tape member 20' in FIG. 1 and the open position as illustrated by tape member 20 in FIG. 1. An end section of the element 30 at its outer extremity remote from the diaper is folded over and joined along part of the pressure sensitive adhesive layer 33 to form a finger tab 36.

Figure 2:
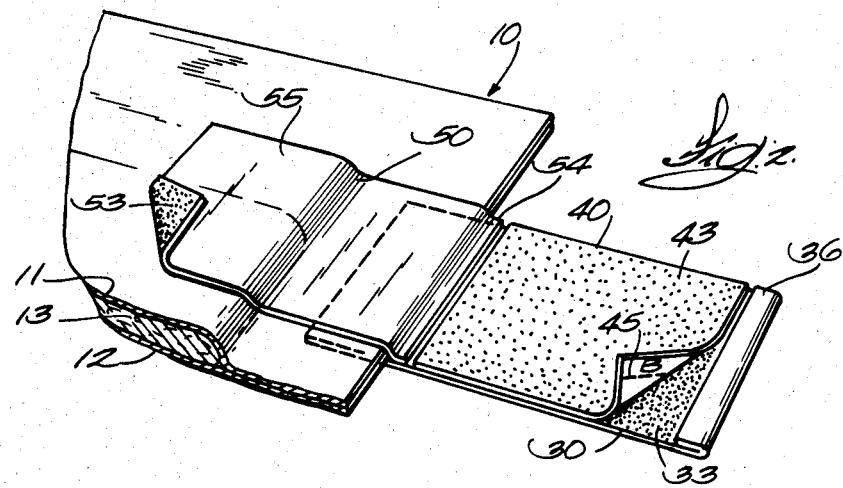
FIG. 2 is an enlarged perspective view of a refastenable tape member.
Figure 3:
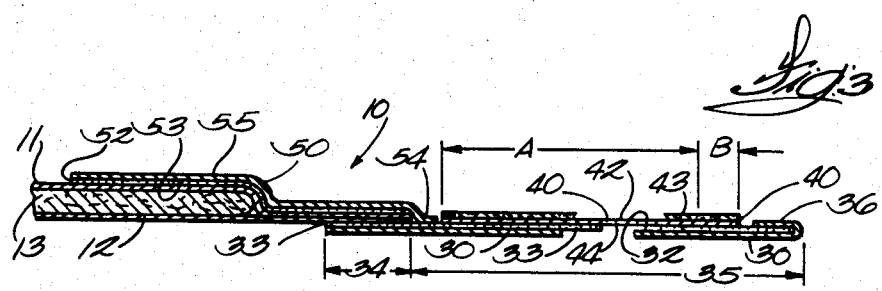
FIG. 3 is a sectional view of a refastenable tape member, with portions broken away to illustrate individual layers and surfaces.

The primary closure tape element 40 is made of a strip of flexible material, such as thermoplastic film or paper, and has a first or upper surface 42 that is covered with a pressure sensitive adhesive layer 43. The second or lower surface 44 of the element 40, opposite from the first surface 42, is releasably joined to pressure sensitive adhesive layer 33 of the secondary closure tape element 30 over the major portion of its area which is identified as portion A in FIG. 3. A minor portion of the area of surface 44 indicated as end marginal portion B in FIG. 3 is to be adhesively bonded to the pressure sensitive layer 33 of the secondary closure tape element 30, the purpose of which will be described hereinafter. Marginal portion B of the surface 44 is also identified in FIG. 2 as the portion extending outboard of dashed line 45; dashed line 45 is shown in FIG. 2 for clarity of description and normally is not present on the surface 44 of the element 40.

Stationary release element 50 of the element 50 of the refastenable tape member 20 comprises a strip of thermoplastic film or paper having a pressure sensitive layer 52 on its first or lower surface 53. The pressure sensitive adhesive layer 52 is adhesively bonded to bodyside liner 11 of the diaper and is fixed in position thereon. As illustrated in FIGS. 2 and 3, the release element 50 may have an end marginal portion 54 that overlaps and is adhesively bonded to the secondary closure tape element 30. The release element 50 has a second or upper surface 55 which is to function as a release surface with respect to pressure sensitive adhesive layer 43 of the primary closure tape element 40 for the purpose explained below.

The term "pressure sensitive adhesive" refers to an adhesive which is aggressively and permanently tacky at room temperature and adheres to other surfaces upon the application of pressure, such as by hand, without requiring other forms of activation. Many suitable formulations of pressure sensitive adhesives are known in the art and may be used for layers 33, 43 and 52. Typical pressure sensitive adhesives include synthetic or natural rubber or a synthetic polymer or copolymer compounded with compatible resin tackifiers such as terpene resins, ester gum, etc., and dispersed in an appropriate solvent such as an organic solvent or water.

The term "adhesively bonded" as used herein to denote the nature of an interfacial bond between an adhesive layer and another surface or layer means that the adhesive layer is adhered or bonded to the other surface or layer firmly enough that the two are held together.

As used herein, the term "releasably joined" to denote the nature of an interfacial bond between an adhesive layer and another surface is defined as meaning that the surface will cleanly separate from the adhesive layer without significant transfer of the adhesive to the surface. Thus for example, the surface 44 of tape element 40 is releasably joined to pressure sensitive adhesive layer 33 of tape element 30 and surface 55 of the element 50 is releasably joined to pressure sensitive adhesive layer 43 of tape element 40 when a tape member is in its closed position. The materials for the elements 30 and 50 should either be inherently releasable with respect to pressure sensitive adhesive or comprise a material having a suitable release coating on its surface in contact with its respective adhesive layer. Surfaces which are to have this release characteristic can be coated or impregnated with suitable low surface energy materials, for example silicone coatings, carbamate coatings based upon the reaction products of polyvinyl alcohol with aliphatic isocyanates, and other types of release coatings which are well known in the art.

The manner of producing the end portion B of the tape element 40 will vary depending on the nature of the material from which the element 40 is made. If the element 40 has a release coating on its lower surface 44, the release coating can be removed by dissolving the coating with a solvent along an end portion B. Also, the release coating can be covered, or masked, along an end portion B. A particularly useful means to accomplish this is to apply a color coating containing a suitable pigment or dye over the release coating along an end portion B. This will mask the release coating and also provide a colored identification or locator for the end portion B. If the surface 40 is a material that is inherently releasable, the end portion B can be treated or coated so that it can adhesively bond to the pressure sensitive adhesive layer 33 of tape element 30. The portion A is to comprise the major portion of the area of surface 44 of element 40, and portion B the minor portion thereof. For optimum results, the area of end portion B is about 15 to 25% of the area of surface 44 of the primary closure tape element 40, most preferably about 20% thereof.

(c) Operational Description

When the diaper 10 is manufactured and packaged ready for use, the refastenable tape members 20 and 20' are both folded to their closed or storage position shown with reference to member 20' in FIG. 1. In the storage position, the secondary closure tape element 30 of each member 20 and 20' is folded over about the adjacent side edge of the diaper and the pressure sensitive adhesive layer 43 of the primary closure tape element 40 of each member contacts and is releasably joined to the second or upper surface 55 of a stationary release element 50. This positions the free end portion 35 of the secondary closure tape element 30 inboard of the diaper and covers the pressure sensitive adhesive layer 43 of the tape element 40. The user withdraws a diaper from a box or other suitable package thereof with the refastenable tape members 20 and 20' in this condition.

To effect the initial closure of the diaper, the user grasps the finger tab 36 of the secondary closure tape element 30 and separates the pressure sensitive adhesive layer 43 of the primary closure tape element 40 from the stationary release element 50. This separation is readily obtained since, as noted previously, the pressure sensitive adhesive layer 43 is releasably joined to the outer surface 55 of the element 50. The user then hinges the secondary closure tape element 30 about the side edge of the diaper to the open position illustrated with respect to the member 20 in FIG. 1. After fitting the diaper about an infant, the rear panel 17 is overlapped with the front panel 18 of the diaper and the primary closure tape element 40 of each refastenable tape member 20 and 20' is adhesively bonded along its pressure sensitive adhesive layer 43 to the outer cover of the front panel 18 in the manner illustrated in FIG. 4. When both members 20 and 20' are joined to the front panels in this fashion, the diaper is securely held about the waist of the infant.

If it is desired to check the diaper at any time after it has been first applied, the mother may grasp the finger tab 36 of the secondary closure tape element 30 and separate the pressure sensitive adhesive layer 33 thereof from the surface 44 of the primary closure tape element 40 merely by lifting the element 30 away from the element 40. Because the pressure sensitive adhesive layer 33 of the secondary closure tape element 30 is releasably joined to the second surface 44 of the primary closure tape element 40, the element 30 is readily separated from the element 40 by this operation. The primary closure tape element 40 remains adhered to the cover 12 of the diaper along the front panel thereof because the adhesive bond between the pressure sensitive adhesive layer 43 to the outer cover 12 is stronger than the releasable joinder bond between the surface 44 and the pressure sensitive adhesive layer 33. Both refastenable tape members 20 and 20' are opened in this fashion, which condition is shown in FIG. 5, so that the diaper can be checked or even removed from the infant. If the diaper is to remain in use, the user then recloses the members 20 and 20' by joining the pressure sensitive adhesive layer 33 of each secondary closure tape element 30 to either the second surface 44 of the primary closure tape elements 40 or to a fresh portion of the exterior of the cover 12 of the front panel. If refastening is accomplished by rejoining the pressure sensitive adhesive layer 33 to the element 40, the diaper may be opened several more times if necessary by repeating the procedure as described. However, if only a second closure of the diaper is required, the secondary closure tape element 30 may be adhered to a fresh portion of the exterior of the cover 12 of the front panel outside of the primary closure tape element 40.

There has thus been described a new refastenable tape system for disposable diapers and similar garments that is useful in providing for two or more openings and refastenings of the garment. The new construction has two important characteristics which are useful in a refastenable tape system. (1) In connection with refastenable pressure sensitive adhesive tape closure means, it is necessary that the primary closure tape release dependably from the stationary release tape element to which its pressure sensitive adhesive layer is attached when the tape closure means is in its closed position. This feature is obtained with the present invention due to the primary closure tape element 40 being adhesively bonded to the secondary closure tape element 30 along its end portion B. This will ensure that the primary closure tape element 40 will remain adhered to the secondary closure tape element 30 when the refastenable tape closure members 20 and 20' are folded to their open position. Greater reliability is obtained because the adhesive bonding of portion B to the tape element 30 is independent of the release characteristic of the upper surface 55 of the stationary release element 50. When the stationary release element is formed of a strip of material coated with a release coating, variations in the release coating will affect the releasability of the primary closure tape from the stationary release element and it can sometimes happen that if an insufficient amount of release coating is on the release element the primary closure tape will not release from it when desired; if this should occur, the primary closure tape element 40 will remain adhered to the element 50 and the refastenability of the system will be destroyed. (2) When the diaper is first closed by means of the primary closure tape element 40 in the manner illustrated in FIG. 4, the adhesive bond between the primary closure tape element and the secondary closure tape element 30 along the end marginal portion B of the former will aid in preventing accidental or premature separation of the primary and secondary tape elements during the initial closure. The prior art systems of which I am aware have the entire surface of a primary tape element releasably joined to an adhesive layer of a secondary tape element so that there will be a greater chance for premature separation of the two elements during the initial closure of the diaper.

The present invention has been described with respect to certain specific embodiments. However, modifications may be made to the described embodiments that are within the spirit and scope of the present invention. For example, the primary closure tape element 50 has been described above as including an end portion B that is to be adhesively bonded to the pressure sensitive adhesive layer 33 of the secondary closure tape element 30. The end marginal portion B may be adhesively bonded to the pressure sensitive adhesive layer 33 along its entire area as illustrated, or it may have a patterned zone that is bonded to the pressure sensitive adhesive layer along spaced discrete portions. Also, the marginal portion B is shown as being an end portion of the primary closure tape element 50 but it may also comprise a side, or edge, portion of the element 40. Still further, the pressure sensitive adhesive layer 43 of the primary closure tape element 40 is illustrated as being releasably joined to the pressure sensitive adhesive layer 30 along its entire area except for the marginal portion B; another alternative would be to provide the surface 44 of the tape element 40 with a patterned adhesive layer so that the element would have discrete spaced zones throughout the area of the surface 44 that would be releasably joined to the pressure sensitive adhesive layer 33 of the tape element 30. It is intended that all modifications of the refastenable tape system described herein and others that would suggest themselves upon review of the present description which are within the spirit and scope of this invention are to be encompassed within the appended claims.

I claim:

1. In a refastenable tape member for disposable garments of the type including a primary tape element for effecting a first closure of a portion of the garment, a secondary tape element for effecting second and any subsequent closures thereof, and a stationary release element secured to the garment and having an exposed surface, the improvement wherein:
(1) the secondary tape element comprises a flexible backing strip and a pressure sensitive adhesive layer on a surface of the backing strip,
a first portion of the pressure sensitive adhesive layer being adhesively bonded to part of the garment, and a second portion of the pressure sensitive adhesive layer extending beyond the part of the garment to which the first portion is bonded;
(2) the primary tape element comprises a flexible backing strip having opposed upper and lower surfaces and a pressure sensitive adhesive layer on the upper surface,
the lower surface of the primary tape element being in contact with the pressure sensitive adhesive layer of the secondary tape element with
a major portion of the area of said lower surface being releasably joined to the pressure sensitive adhesive layer of the secondary tape element, and
a minor portion of said lower surface being adhesively bonded to the pressure sensitive adhesive layer of the secondary tape element; and
(3) the refastenable tape member being foldable between (i) a storage position in which the pressure sensitive adhesive layer of the primary tape element is releasably joined to the exposed surface of the stationary release element and (ii) an open position wherein the pressure sensitive adhesive layer of the primary tape element is separated from the stationary release element and exposed for effecting the first closure of the garment, the secondary tape element being releasable from the lower surface of the primary tape element when in its first closure condition to thereby expose pressure sensitive adhesive layer of the secondary tape element for effecting second and subsequent closures of the garment.

2. A refastenable tape member according to claim 1 wherein: the minor portion of the lower surface of the primary tape element is about 15 to 25% of the area of the lower surface of the primary tape element.

3. A refastenable tape member according to claim 1, wherein: the minor portion of the lower surface of the primary tape element is about 20% of the area of said lower surface.

4. A refastenable tape member according to claim 1 wherein: the minor portion of the lower surface of the primary tape element adhesively bonded to the pressure sensitive adhesive layer of the secondary tape element comprises an end portion of said lower surface.

5. A refastenable tape member according to claim 1, 2, 3 or 4 wherein:
the lower surface of the primary tape element is coated with a release coating, and the release coating is masked along the minor portion thereof.

6. A refastenable tape member according to claim 1, 2, 3 or 4 wherein:
only the major portion of the lower surface of the primary tape element is coated with a release coating.

7. A refastenable tape member according to claim 1, 2, 3 or 4 wherein:
the minor portion of the lower surface of the primary tape element is colored.

8. A refastenable tape member according to claim 1, 2, 3 or 4 wherein:
the second portion of the secondary tape element includes an end section remote from the garment that is folded over and joined to the pressure sensitive adhesive layer of the secondary tape element to form a finger tab.

* * * * *